United States Patent [19]
Janik et al.

[11] Patent Number: 6,128,080
[45] Date of Patent: Oct. 3, 2000

[54] EXTENDED RANGE INTERFEROMETRIC REFRACTOMETER

[75] Inventors: Gary R. Janik, Palo Alto; Douglas W. Shepard, Santa Barbara; Steven P. Trainoff, Carpinteria; David T. Phillips, Santa Barbara, all of Calif.

[73] Assignee: Wyatt Technology Corporation, Santa Barbara, Calif.

[21] Appl. No.: 08/870,937

[22] Filed: Jun. 6, 1997

[51] Int. Cl.[7] .................................................. G01B 9/02
[52] U.S. Cl. ............................................ 356/351; 356/361
[58] Field of Search ................................... 356/346, 349, 356/351, 761

[56] References Cited

U.S. PATENT DOCUMENTS 4,229,105 10/1980 Silvergage .
5,663,793 9/1997 de Groot ................................. 356/351

FOREIGN PATENT DOCUMENTS 2697336 4/1994 France .

OTHER PUBLICATIONS

Collins, Robert W. and K. Vedam, *Ellipsometers*, Encyclopedia of Applied Physics, 1993, selection, vol. 6, VCH Publishers, Inc.

*Primary Examiner*—Robert H. Kim
*Assistant Examiner*—Andrew H. Lee
*Attorney, Agent, or Firm*—Philip J. Wyatt

[57] ABSTRACT

A method and apparatus is disclosed for measuring the refractive index difference between a reference and sample liquid based on an interferometric design. The resultant device has an almost unlimited range of operation in contrast to a conventional interferometric refractometer of the so-called polarization type whose dynamic range is restricted to a relatively narrow range of refractive indices. The measurement of the refractive index difference between a sample and reference cell is achieved by measuring the angle through which the plane of polarization of a combined beam has rotated. For the conventional device, this angle is restricted to about $\pi$ radians which corresponds to a half wavelength shift between the reference and sample components of said combined beam. The extended range device disclosed permits this angle to be tracked and measured accurately over many rotations. The rotation tracking is achieved by one of three embodiments, the preferred of which involves the use of a liquid crystal retarder. The other two techniques incorporate, respectively, a rotating polarizer and a doubly split beam. All three embodiments permit the measurement of both the sine and cosine of the rotation angle and, thereby, allows a four quadrant arctangent calculation to yield the rotation angle directly. The error associated with such measurements is not a function of the rotation angle of the combined beams.

19 Claims, 8 Drawing Sheets

EXTENDED RANGE INTERFEROMETRIC REFRACTOMETER

BACKGROUND AND NEED FOR THE INVENTION

Differential refractometers are widely used as detectors for the chromatographic analysis of a broad range of chemical compounds including polymers, pharmaceuticals, and food products. Concentrations of solutes of $10^{-6}$ to $10^{-8}$ g/ml are commonly detected. Differential refractometers produce a signal which is proportional to the difference of the refractive index between at sample and a reference solution. The reference is usually a pure solvent. In the limit of vanishingly small solute concentration dc, the variation of the sample refractive index dn is defined to be dn/dc. This value is dependent on both the dissolved compound and the solvent, and must be determined in order to relate the instrument refractive index change to the instantaneous solute concentration. Once the value of dn/dc is known at a particular wavelength for a particular compound and solvent, the refractometer can be used as an absolute concentration detector. If the instrument response is $\Delta n$, then the solute concentration change above that of the pure solvent $\Delta c$ is related simply by $\Delta c = \Delta n/(dn/dc) + O(\Delta n^2)$.

During the past 20 years, there has been increased interest in the use of light scattering to measure molar mass during chromatographic analysis. The first combination of an on-line chromatographic separation combined with a refractive index detector and light scattering detector was preformed in 1974 by Ouano and Kaye (J. Poly. Sci. A-1, volume 12, page 1152). The amount of light scattered into small scattering angles is directly proportional to the product of molar mass; times concentration. Thus by dividing the light scattering signal by the concentration signal, the molar mass of each eluting fraction may be determined. Since the refractive index increment, dn/dc, also appears in the light scattering equations, it should be measured at the same wavelength as the light scattering measurement. There has always been a need for an accurate refractometer that is sensitive enough to serve as a chromatographic detector, and has a sufficiently wide range to measure dn/dc at both convenient laboratory concentrations and the very low concentrations associated with HPLC separations. Unfortunately, for reversed phase chromatography, the refractive index change of the solvent gradient itself will often drive the differential refractive index detector off scale. For many types of HPLC separations, the concentration variation among the separated peaks is so great that for some peaks the refractive index responses saturate the RI detector while for others, the response may be so low as to be undetectable. Therefore there is a need for a refractometer with great sensitivity and great dynamic range. Most refractometers increase the dynamic range at the expense of decreased sensitivity or vice versa.

Most of the existing commercial refractometers are based directly on Snell's Law of Refraction, $$n_1 \sin(\theta_1) = n_2 \sin(\theta_2) \tag{1}$$

which relates the refractive index of two materials, with refractive index $n_1$ and $n_2$, to the refraction of a light beam striking the interface between the materials. The usual instrument design forms the sample into a prism to deflect a light beam, and then uses an opposed prism of reference material to refract it back. Any net deflection of the beam then indicates the presence of the sample material.

Another type of refractometer measures the intensity of light reflected from the liquid-glass interface of a sample cell relative to a beam reflected from the liquid-glass interface of the reference fluid. Based on Fresnel's laws of reflection at such an interface, the incident beams are normally oriented to strike the interfaces close to the critical angle The reflected beams are then focused onto the surface of a dual element photodetector for subsequent amplification and recording. Such refractometers also have a rather limited linear range. Although intensity based refractive index detectors are available, the deflection type still remains the most common.

An interferometric refractometer has long been considered the ideal device by which refractive index changes may be measured. The interferometer compares the optical phase shift of equal length light beams in the sample and reference cells. The phase difference in radians is $\phi$ where:

$$\phi = 2\pi(n_1 - n_2)L/\lambda \tag{2}$$

L is the length of the cell and $\lambda$ is the wavelength of light in vacuum. This measurement is a linear function of the refractive index difference, and the calibration constant is the same for any solvent refractive index. The interferometric refractometer produces a signal based upon the interference of two beams which have traversed separate paths corresponding to a reference material and a sample material. As long as the contrast between these combining beams remains high, the interferometer will present a series of fringes corresponding to a generally enhanced range of refractive indices measurable. Because of the broad operating range associated with the multi-pathlengths and the inherent sensitivity of the interferometric measurement, such interferometric refractometers have been developed to overcome many of the disadvantages of the deflection method.

A practical interferometric refractometer is the "polarization interferometer" or "wave shearing interferometer". This device is referred to as "Smith's Polarization Interferometer" in some texts, and it was first commercially produced in Sweden by Biofoc AB in the 1970's. During the 1980's it was developed and sold by the Swedish company Tecator under the trade name Optilab. Some elements of its flow cell design are described in Silverbage's U.S. Pat. No. 4,229,105. Since about 1992, the instruments have been manufactured by Wyatt Technology Corporation of Santa Barbara Calif. who have improved the design further. In the discussion below, we refer to the differential refractometer based on Smith's Polarization Interferometer as the "Optilab".

The Optilab differential refractometer uses a tungsten light source whose collimated beam is linearly polarized at 45 degrees to the optical axes of a Wollaston prism which then divides it into two orthogonal linearly polarized beams. The diverging beams are made parallel by a lens. The vertically polarized beam passes through the sample cell while the horizontally polarized beam passes through a parallel reference cell. The transmitted beams are then recombined by another lens and a second Wollaston prism. A quarter wave retarder is then used to convert each of the linearly polarized components into circularly polarized light. The vertically polarized beam becomes circularly polarized clockwise and the horizontally polarized beam becomes circularly polarized counterclockwise. The resulting superposition of counter-rotating circular waves add to produce an elliptically polarized beam. Ideally, the minor axis is zero and the beam is linearly polarized. In practice, the quarter waveplate shift is not exactly 90°. The rotation of the major axis of the ellipse is measured. The angle of the axis rotates relative to the initial 45° linearly polarized beam at half the phase shift introduced by the difference between the sample and reference cells, i.e.

$$\theta = \phi/2, \quad (3)$$

where $\theta$ is the angle of the major axial polarization and $\phi$ is given by Eq. (2).

This remarkable result means that the optical phase shift of the interferometer produces a physically measurable angle of polarization. In the Optilab instrument, the elliptically polarized beam is transmitted through a polarization analyzer, a narrow band interference filter, and then on to a silicon photodiode detector. In the ideal, linearly polarized case, assuming the analyzer angle is zero, the resulting signal intensity I varies sinusoidally as:

$$I = I_0 \cos^2\theta = \tfrac{1}{2} I_0 [1 + \cos\phi]. \quad (4)$$

The reference intensity scale $I_0$, can be established by physically rotating the analyzer to measure the maximum and minimum intensity values.

The most linear part of the signal is near $I = \tfrac{1}{2} I_0$, where $\cos(\phi) = 0$. Shifting the signal intensity axis up to $\tfrac{1}{2} I_0$, and the phase axis 90° by rotating the analyzer, the shifted phase angle $\phi' = \phi + \pi/2$. Define the shifted intensity $I_S = 2I - I_0$ so that one has $$I_S = I_0 \sin\phi' = I_0 \phi' + O(\phi'^3) \quad (5)$$

$$\therefore I_S/I_0 \approx I_0 2\pi(n_1 - n_2)L/\lambda \quad (6)$$

for small values of $\phi'$.

At the limit of its sensitivity, the Optilab provides a linear signal proportional to the refractive index difference, with sensitivity determined by cell length L, optical wavelength in vacuum $\lambda$, and a simple intensity normalization based on rotating the polarization analyzer to determine $I_0$. A later model, the Wyatt Optilab-DSP, uses a microprocessor to compute the arcsine for Eq. (5) and thus extends the linear range slightly. The microprocessor also controls the motion of the polarization analyzer.

Optilab manufacturers have met the need for both highly sensitive chromatographic measurements and wide range dn/dc measurements by offering several cells of different lengths, L. Normally dn/dc measurements are made with a 0.2 mm long cell, and chromatographic measurements use cells or 1 or 10 mm in length. The cells are expensive and require some re-plumbing to change.

Wavelengths corresponding to lasers used in light scattering instruments, such as the DAWN-DSP multiangle light scattering photometer manufactured by Wyatt Technology Corporation of Santa Barbara Calif., include 690 nm, 633 nm, 514 nm, and 488 nm. Other wavelengths are easily provided by changing the internal interference filter and quarter wave plate to the desired wavelength and adjusting the optics accordingly.

It is possible to use the direct Optilab signal to measure very large changes in refractive index, providing that one can follow the signal through the many fringes that could occur, computing the arcsine as one goes. This method is ambiguous at the peaks of the refractive index signal, since there is no certain indication that the slope of the signal has reversed. Some workers such as Van Hook at the University of Tennessee have used several instruments with different wavelengths of light to help resolve the ambiguity. Details may be found in the paper by M. Smith and W. A. Van Hook in Z. Naturforschung, volume 44A, pages 371 to 375 (1989). The key to using the Optilab at a single wavelength for measuring large refractive index changes is having the ability to measure the rotating angle of polarization of the exiting beam over many rotations. Of course this is a familiar problem in many types of interferometric instruments, and a familiar solution is to use a "quadrature" signal, a cosine to accompany the sine, and thus resolve the ambiguity of direction. Ideally, we seek a refractometer of the Optilab type that is comprised of a single high sensitivity cell, such a the 10 mm cell, that can be used both for high sensitivity chromatography detection, and for low sensitivity dn/dc measurements, and can be used also for gradient reversed phase chromatography where the refractive index of the mobile phase solvent varies over a wide range during the chromatographic separation. Such an "Extended Range Optilab" would meet the need for chromatography detection, gradient chromatography detection and dn/dc measurement in a single instrument.

PRIOR ART

In 1990, Phillips and Borchard (European Polymer Journal volume 26, pages 1289–1294) felt that they had found a means to measure very large phase changes and the associated refractive index difference with an Optilab instrument for the case where the injected sample has a concentration plateau. Although their article indicates some confusion as to the elements of the Optilab interferometer (they forgot to mention the polarization of the incident beam, the analyzer and the proper location of the interference filter), they select an example whose plateau is sufficiently distant from the peaks of the refractive index signal so that they may calculate the refractive index difference from the relation $$\Delta n = (i + \alpha/360°)\lambda/L, \quad (7)$$

where i is the number of fringes before the plateau is reached, $\lambda$ is the vacuum wavelength of the interference filter and a is the increment beyond the last fringe corresponding to the plateau. The authors point out that one still has to decide from the appearance of the trace whether $\alpha$ is between a minimum and maximum or vice versa. Even though this method may be of use in measuring a large refractive index difference of a sample sufficient to produce a plateau, the technique cannot be used to monitor the instantaneous refractive index changes following a chromatographic separation. This would be especially true for the case of an increasing solvent refractive index characteristic of reversed phase chromatography. Indeed, the Phillips et al. approach will only be successful if a single plateau is obtained and the sample is not fractionated before the measurement. Once again, we see the need to measure unambiguously the $\alpha$ and i of Eq. (7) for the general case of arbitrarily changing refractive index.

The closest prior art is a recent invention by Frot, Beauducel, Gonzalez and Couillard, U.S. Pat. No. 5,483,344, which overcomes the refractive index ambiguity by phase modulating one path by means of a Pockel cell and means to follow the interference of a recombined two beam system to track, thereby, the phase difference between the two paths. They begin by using the front end similar to the Optilab structure including a Wollaston or similar beam splitting device to split an incident laser beam into two coherent components. The plane polarized laser beam, probably polarized at 45° to the Wollaston optical axes, passes through a Pockels cell before entering the Wollaston. Suitably oriented, the Pockel cell modulates, thereby, one of the two orthogonal components of the incident laser beam before entry into the Wollaston. Each beam has, therefore, the same intensity, though one is modulated. By means of a half wave plate, the polarization of one of the beams is rotated 90°. This results in the two beams having the same polarization and interfering with one another in a simple manner. The single detector, which intercepts the combined beams, responds simply to the phase difference of the two beams upon which has been superimposed the modulation of the phase of one beam. Following the teaching of Allington, U.S. Pat. No. 4,289,403, the optical path difference may be extracted from measurement of the phase shift at the detector relative to the modulation applied to one of the beams by the Pockel cell. The main problem with this structure is the non-symmetry of the recombining two beams because of the half wave plate placed into one of them. The half wave plate may remove some light from the beam in which it lies. In addition, each beam has a different path length since one contains the half wavelength rotator. Finally, the phase shift of a Pockels cell drifts with temperature. Since only one beam goes through the Pockels cell, there is no easy method for drift cancellation. A major advantage of the Optilab design is the symmetry of both paths which permits more uniform control of possible environmental effects such as temperature and pressure. Frot et al. stress this need for symmetry yet ignore the fact that their own invention includes asymmetric paths.

Frot et al. point out that all earlier type of interferometric device by Couillard, U.S. Pat. No. 4,787,746, whose design objectives were similar to theirs and which used a Piezo electric modulator, will not be as stable since the latter can drift due to heating and cause a resultant drift in the measurement with time. They associate the mechanical motion of the Piezo electric driven mirror as being a potentially unpredictable and non compensated heat source. In addition, the Couillard device uses two detectors, each of which must be calibrated.

There are numerous other references to interferometric approaches for measuring the refractive index values of liquids relative to a reference liquid and they may be found cited in the above referenced U.S. patents.

BRIEF DESCRIPTION OF THE INVENTION

The preferred embodiment of the invention carries out the essential concept of tracking the rotation of the recombined beam's major axis plane of polarization over many cycles, not only in the presence of absorption, but with the characteristic instabilities of laser sources, as well. The original Optilab utilized 10 mn wide narrow band filters to produce nearly monochromatic light. This resulted in fringes which lose contrast and amplitude by about a factor of two over 20 fringes. Lasers provide a convenient source of brighter light with a much narrower spectral width. With a laser source, the fringe amplitude is essentially constant over a hundred or more fringes, and so laser sources are preferred for the invention. Nevertheless, if the anticipated range of refractive index change is not too large, the earlier use of an incandescent or other continuous light source together with an interference filter is still practical.

The preferred approach is to rotate the polarization angle of the combined light beam's major axis using an electrically variable liquid crystal retarder plate. Thus the polarization analyzer is fixed and the polarization angle of the beam is rotated. By electrically scanning the retardance, the maximum and minimum intensity points may be found and the intensity $I_0$ measured. In this way it is possible to locate drive voltages for the retarder which correspond to sine and cosine signals. Then with just a single detector and no moving parts it is possible to switch rapidly back and forth from sine to cosine. Although the four quadrant arctangent $$\arctan [\sin \phi, \cos \phi] = \phi \quad (8)$$

could be used to compute the polarization angle as well as the correct quadrant, given the sine and cosine values, tie actual determination may be improved by making measurements optimally at four angles or more, as will be readily apparent from the detailed description of the invention which follows. On this basis, not only is the precision of the derived phase angle increased, but effects of absorption and laser power drift are anticipated and corrected. However, as more angles are included in the measurement, the measurement time required increases correspondingly. Also, the retardance of the liquid crystal must be measured at each measured voltage.

The invention allows the user to do both high sensitivity chromatography detection and low sensitivity dn/dc measurements without need for extra cells. Its large dynamic range will facilitate the measurement of trace residues in the presence of much larger amounts of major components. By providing high incremental sensitivity over a wide range of refractive indices it is possible to detect low levels of sample materials in the presence of a smoothly changing baseline caused by a gradient between two mobile phase components in a reverse phase chromatography analysis. During unusual intervals with an extremely high rate of refractive index change, it is possible to monitor a single phase angle and simply count fringes, returning to the multiple phase measurement method once the rate of change has slowed down sufficiently.

There are two other implementations of this invention using a split beam and a rotating polarizer, respectively.

DETAILED DESCRIPTION OF THE INVENTION

The Standard Optilab Interferometer Refractometer

Figure 1:
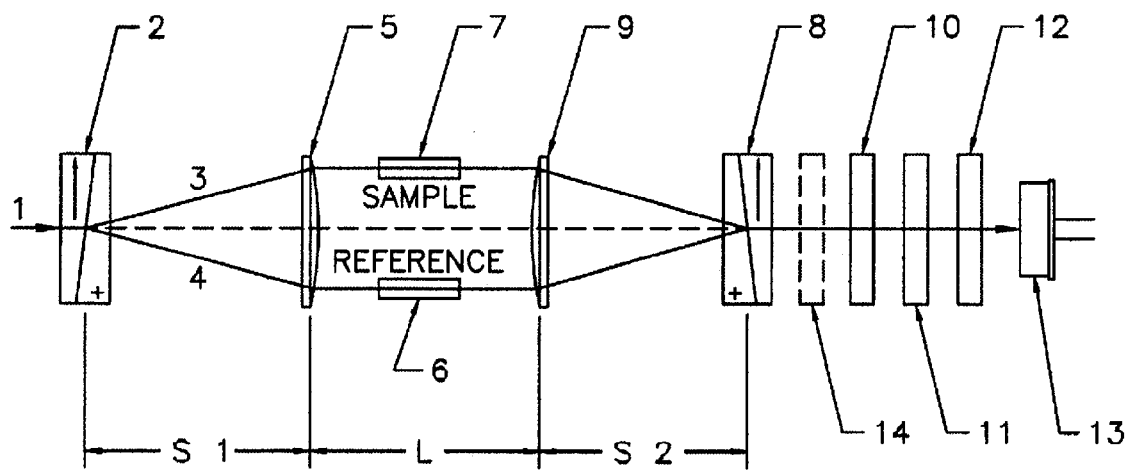
FIG. 1. The original Optilab with the liquid crystal retarder which extends its operating range indicated by the dotted element 14.

The analysis of the basic Optilab interferometer refractometer is well covered by the Optilab documentation provided with the instrumentation by the manufacturer, Wyatt Technology Corporation. Referring to FIG. 1, we see the basic elements of the Optilab structure. The incident collimated light beam 1 is polarized at an angle of 45° to the fast axis of a Wollaston prism 2 which splits the transmitted beam into two orthogonally polarized beams 3 and 4 of equal intensity. These diverging beams are then refracted to parallelism by lens element 5 to pass through reference cell 6 and sample cell 7. The beam passing through the sample cell is vertically polarized while that passing through the reference cell is horizontally polarized. On exiting the cells, the two parallel beams are refracted to focus at the second Wollaston prism 8 by means of a second lens element 9. The combined beam is then passed through a quarter waveplate 10 from which the emerging beam passes through the analyzer 11. If the light source is not monochromatic, which is the case for the traditional Optilab design whose source is generally an incandescent bulb, then all interference filter 12 follows the analyzer to select the specific wavelength at which the measurement is to be made. The beam then passes to a detector means, such as a high gain photodiode or photomultiplier, 13. Naturally, the positions of the two lens elements will have to be changed as the wavelength is changed. The analyzer is generally set at an angle $\phi_0$ with respect to the incident 45° angle of the incident plane of polarization.

Recall from Eq. (2) that the interferometer generates a beam of elliptically polarized light whose major axis polarization angle is related of the optical path difference in the two arms, d, by $$\theta = \pi d/\lambda = \pi(n_1-n_2)L/\lambda = \pi \Delta n L/\lambda, \quad (9)$$

where $\lambda$ is the wavelength of light in vacuum, $\Delta n$ is the index of refraction difference between the two arms and L is the length of the cell. The Optilab measurement of the index of refraction reduces to trying to measure $\theta'=\theta-\theta_0$ where $\theta_0$ is the angle between the exit analyzer and the major axis of polarization of the light beam before the measurement is made. Ideally, $\theta_0=0$, but due to imperfections in manufacturing and optical components, it is generally non-zero. In the standard Optilab, $\theta_0$ is adjusted by rotating the exit analyzer to insure the greatest range of response of the instrument since $\theta'$ itself can vary from $-\pi/2$ to $\pi/2$. For the present invention, the exit analyser is fixed and $\theta_0$ is simply measured before the data ran and subtracted. Therefore, in the discussion which follows, we shall replace $\theta'$ by $\theta$ throughout since $\theta_0$ is always known.

As mentioned earlier, because of imperfect optics, the beam incident on the analyzer does not have a perfectly linear polarization; it is slightly elliptical and, therefore, the intensity which is incident on the photodetector 13 can be expressed in terms of the maximum and minimum intensities, $I_{max}$ and $I_{min}$ as $$I = I_{\min} + (I_{\max} - I_{\min})\cos^2\theta \quad (10)$$

$$= \frac{I_{\max} + I_{\min}}{2} + \frac{I_{\max} - I_{\min}}{2}\cos(2\theta) \quad (11)$$

$$= I_0[1 + C_r\cos(2\theta)] \quad (12)$$

where $I_0$ is the mean intensity of the interferometer output $I_0=(I_{max}+I_{min})/2$ and $C_r=(I_{max}-I_{min})/(I_{max}+I_{min})$ is the so-called contrast ratio of the instrument. The Optilab microprocessor inverts the previous expression to extract $\Delta n$ from Eq. (9)

$$\theta = (\tfrac{1}{2}) \cos^{-1}[(I/I_0-1)/C_r]. \quad (13)$$

There are two problems which are immediately apparent. The most obvious is that this expression only determines the angle between $-\pi/4$ and $\pi/4$. From a single measurement, one cannot determine the (quadrant of the angle. This limits the angular measurement to less than a fringe. In fact, the Optilab limits its angular range to a maximum of 140°. The second problem is that the sensitivity goes to zero when the argument of the arccos gets near ±1. This occurs when the intensity is near $I_{max}$ or $I_{min}$. One can understand this quantitatively by analyzing the error propagation in this equation to determine the error in the measurement of the photodetector intensity. The photodetector assembly has some intrinsic intensity fluctuation $\sigma_i$. From the standard formula for the propagation of errors, one finds the error in a quantity $f(x_1, \ldots, x_i)$ that depends on the i measurements whose random errors are $\sigma_i$ may be computed from $$\sigma_f^2 = \sum_i \left(\frac{\partial f}{\partial x_i}\right)^2 \sigma_i^2 \quad (14)$$

where there are as many terms as there are variables which have random errors. Since the only fluctuating variable is the intensity, this reduces to an error in the angle measurement of $$\sigma_\theta = \frac{1}{2C_r}|\csc(2\theta)|\sigma_I. \quad (15)$$

Therefore, when $\theta \sim 0$ or $\pi$, $\sigma_\theta \to \infty$. The problem of decreasing sensitivity can be solved if one has more information than the simple cosine in Eq. (12). This observation forms the basis of the present invention which is directed to extending the range of the basic Optilab instrument.

Extended Range Implementation: Liquid Crystal Retarder

The extended range instrument measures the polarization angle of the light by measuring both the sine and the cosine of the intensity. This is accomplished by means of a liquid crystal retarder 14, of the type manufactured by Meadowlark Optics, Inc., placed in the light path of the combined beam between the second Wollaston prism 8 and the quarter wave plate 10. The placement of the liquid crystal retarder is indicated by the dotted element 14 in FIG. 1. Its fast axis is aligned with the vertical polarization axis of the light passing through the sample side of the cell. The slow axis is, of course, aligned with the horizontal polarization axis of the reference side. It should be noted that the liquid crystal retarder could be placed also, with the same orientation, between the incident plane polarized light source and the first Wollaston prism 2.

In response to a 2 kHz amplitude modulated square wave voltage, the liquid crystal varies the retardance between die fast and slow axes. This creates an additional path difference between the two sides of the cell. The relationship between the retardance and the amplitude of the square wave is strongly nonlinear but it is monotonically decreasing from a maximum retardance when 0 voltage is applied to a minimum retardance when the maximum voltage is applied (approximately 40 V peak-to-peak). Because of the non-linear response of the liquid crystal retarder, it is helpful to use a compensating non-linear digital to analog converter to control the retarder.

During the calibration of the retarder, two voltages are found which give retardance difference of exactly $\lambda/4$. Let the retardance of the two states be $r_1$ and $r_2=r_1+\lambda/4$, respectively. After the beam passes through the quarter wave plate, the light is elliptically polarized with major axis angles $$\theta_1 = \pi \frac{d+r_1}{\lambda} \quad (16)$$

-continued $$\theta_2 = \pi \frac{d+r_2}{\lambda}$$
$$= \theta_1 + \frac{\pi}{4}.$$

where $\theta_1=\theta+\theta_r$, $\theta$ is the polarization angle we are trying to measure, and $\theta_r$ is a constant additional rotation introduced by the liquid crystal. The intensity measurements of the two states are $$I_1/I_0 = 1 + C_r\cos(2\theta_1) \qquad (17)$$

$$I_2/I_0 = 1 + C_r\cos(2\theta_1 + \pi/2)$$
$$= 1 - C_r\sin(2\theta_1)$$

One may now use the two measurements to compute both the contrast ratio and the polarization angle (assuming $I_0$ is constant) as $$\cos(2\theta_1) = \frac{I_1/I_0 - 1}{C_r} \qquad (18)$$

$$\sin(2\theta_1) = -\frac{I_2/I_0 - 1}{C_r}.$$

Note that these expressions preserve the sign of both the sine and cosine. Therefore one may determine the angle by performing a four quadrant arctangent which preserves the information about the magnitude of the polarization angle as well as the quadrant, i.e.

$$\theta_1 = \arctan[\sin(2\theta_1), \cos(2\theta_1)]/2 \qquad (19)$$
$$= \arctan[-I_2/I_0 + 1, I_1/I_0 - 1]/2$$

and $\theta_1$ is independent of the contrast ratio. The second line follows from the first since the arctangent depends only on the ratio of the two arguments. The crucial point is that this expression gives the polarization angle which lies within the full range of $-\pi/2$ to $\pi/2$. One also may compute explicitly the contrast ratio from Eq. (18) by squaring both expressions and adding them to give $$C_r^2 = (I_1/I_0-1)^2 + (I_2/I_0-1)^2. \qquad (20)$$

In summary, one can compute both $\Delta n$ and $C_r$ for every measurement. The contrast ratio depends on the alignment of the optics, the quality of the optical components, the absorption of the beam in the cell, the size of the cell, and the temperature difference between the reference and sample cell. Since the optics do not change during the course of the measurement, it is also possible to extract the optical absorption of the sample from $C_r$.

Figure 2A:
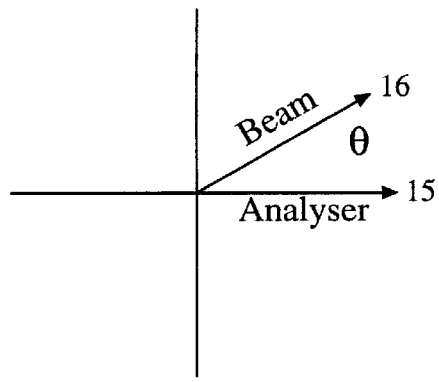
FIG. 2. A phase diagram of the measured signal showing details of the measurement FIG. 3. An elution chromatograph showing the measured refractive index of a reversed phase gradient superimposed upon an eluting sample.
Figure 2B:
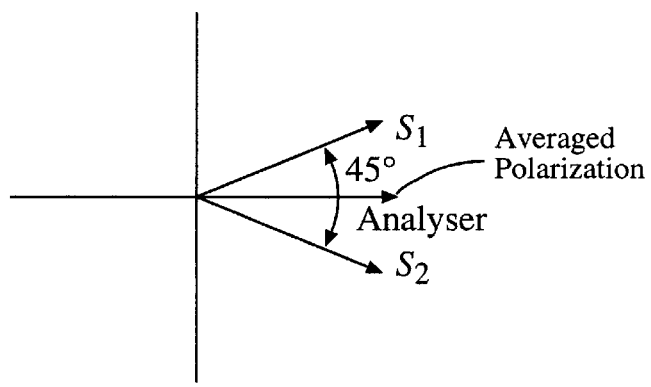
Figure 2C:
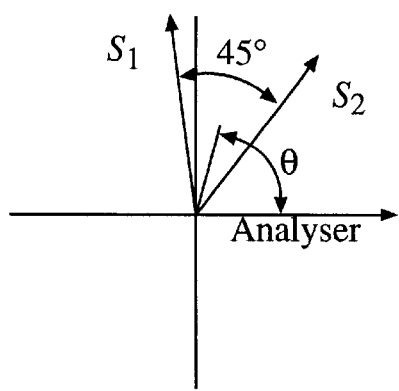

FIG. 2a shows the relative positions of the analyzer axis 15 and the incident beam plane of polarization 16 during the calibration step. After calibration, the retarder produces two beam polarizations $S_1$ aid $S_2$ as shown in FIG. 2b where the combined beam polarization either lies along $S_1$, corresponding to zero retardance, or along $S_2$, corresponding to a 45° redardance. The angular separation between the retarded and non-retarded beam polarizations is 45°, as shown, with polarizations $S_1$ and $S_2$ lying symmetrically above and below, respectively, the analyzer axis at 22.5° therefrom. FIG. 2c shows the two beams for the general case where the major axis plane of polarization of the combined beam, $S_1$, lies at an angle $\theta$ with respect to the analyzer axis and the retarded beam $S_2$ lies at an angle of 45° with respect to $S_1$.

Fringe Tracking

Of course, the measurement of the angle $\theta_1$ is still uncertain up to an uncertainty of $2n\pi$ where n is an integer. This is simply a statement that one does not know from this measurement which fringe the instrument is measuring. Fortunately, this is easy to determine from the sequence of measurements, if one assumes that the angle doesn't change by more than half of a fringe between two successive measurements. Denote the sequence of angular measurements $\theta_i$. If one makes the assumption that $$\theta_i - \theta_{i-1} \leq \pi/2, \qquad (21)$$

then one may track the angle including rotations. It is best explained by defining a winding number as $w=\phi/2\pi=\theta/\pi$, where $\theta$ is the total angular change of the polarization angle since the beginning of the measurement. The integer portion of the winding number is the number of fringes which have been observed. The winding number may be calculated from the sequence of angular measurements by $$w_{i+1} = w_i + \left\{\left[\left(\frac{\theta_{i+1}}{\pi} - w_i \bmod 1\right) \bmod 1\right] + \frac{3}{2}\right\} \bmod 1 - \frac{1}{2}. \qquad (22)$$

This expression requires some explanation. The term $\theta_{i+1}/\pi$ computes the current fractional winding number in the range $(-\frac{1}{2}, \frac{1}{2})$. The expression $(\theta_{i+1}/\pi - w_i \bmod 1) \bmod 1$ is the difference between the current fractional winding number and the previously accumulated value. This difference is restricted to the range $(-\frac{1}{2}, \frac{1}{2})$. By adding $\frac{3}{2}$, one has the difference+$\frac{3}{2}$ in the range $(1, 2)$. Performing the final modulus gives the difference+$\frac{1}{2}$ in the range $(0,1)$. Subtracting the final $\frac{1}{2}$ yields the difference in the range $(-\frac{1}{2}, \frac{1}{2})$. Then this difference is added to $w_i$. The final value of $w_{i+1}$ is guaranteed to have the same fractional portion as $\theta_{i+1}/\pi$. Mathematically one has $$w_{i+1} \bmod 1 = \theta_{i+1}/\pi \bmod 1, \qquad (23)$$

as can be seen by taking the modulus of both sides of Eq. (22). The reason for this somewhat convoluted form is that it is insensitive to numerical round off error even when the difference between successive measurements is small. The number of bits required to accurately represent each intermediate value is always less than the number of bits required for the final result.

Error Not a Function of Angle

The significant advantage of the measurement technique of this invention is that the error associated with the measurement no longer diverges. It can be computed explicitly as $$\sigma_\theta = \sigma_I[2I_0^2 - 2I_0(I_1 + I_2) + I_1^2 + I_2^2]^{-\frac{1}{2}} \qquad (24)$$
$$= \frac{\sigma_I}{I_0 C_r}.$$

This expression is independent of $\theta$! The measurement error does not vary as a function of angle, unlike the original Optilab.

Data

Figure 3:
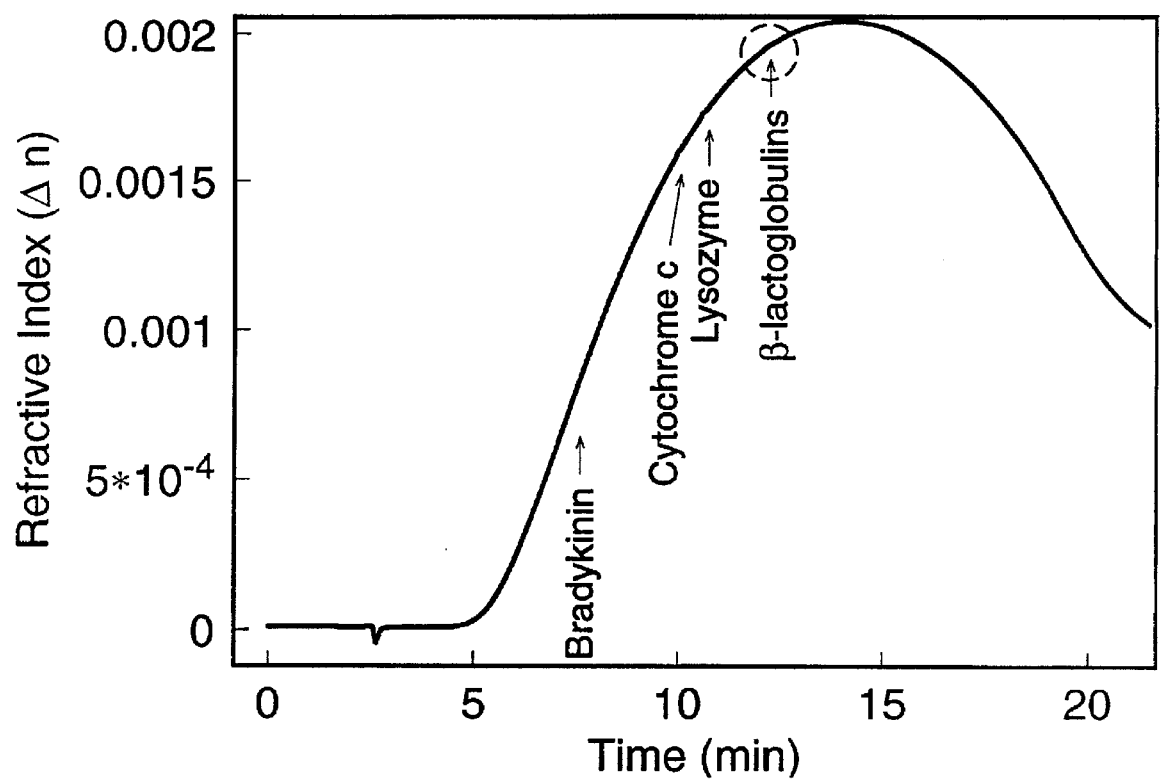
Figure 4:
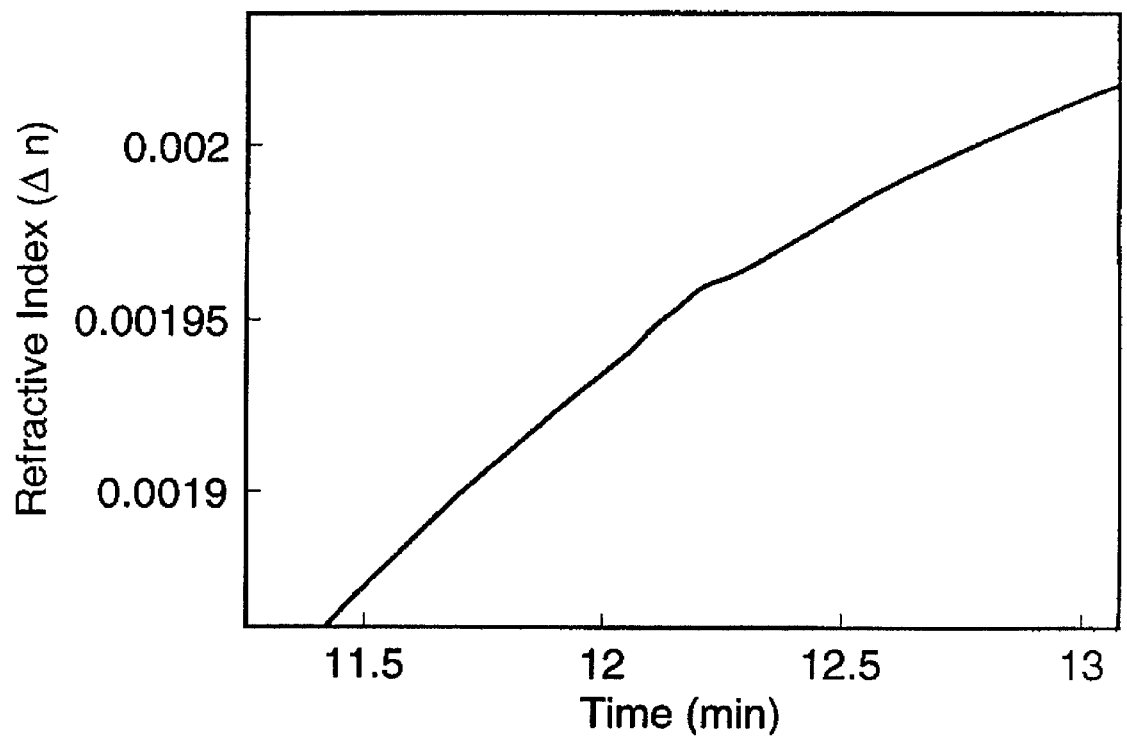
FIG. 4. The enclosed section of FIG. 4 enlarged to show eluting species superimposed on the gradient.
Figure 5:
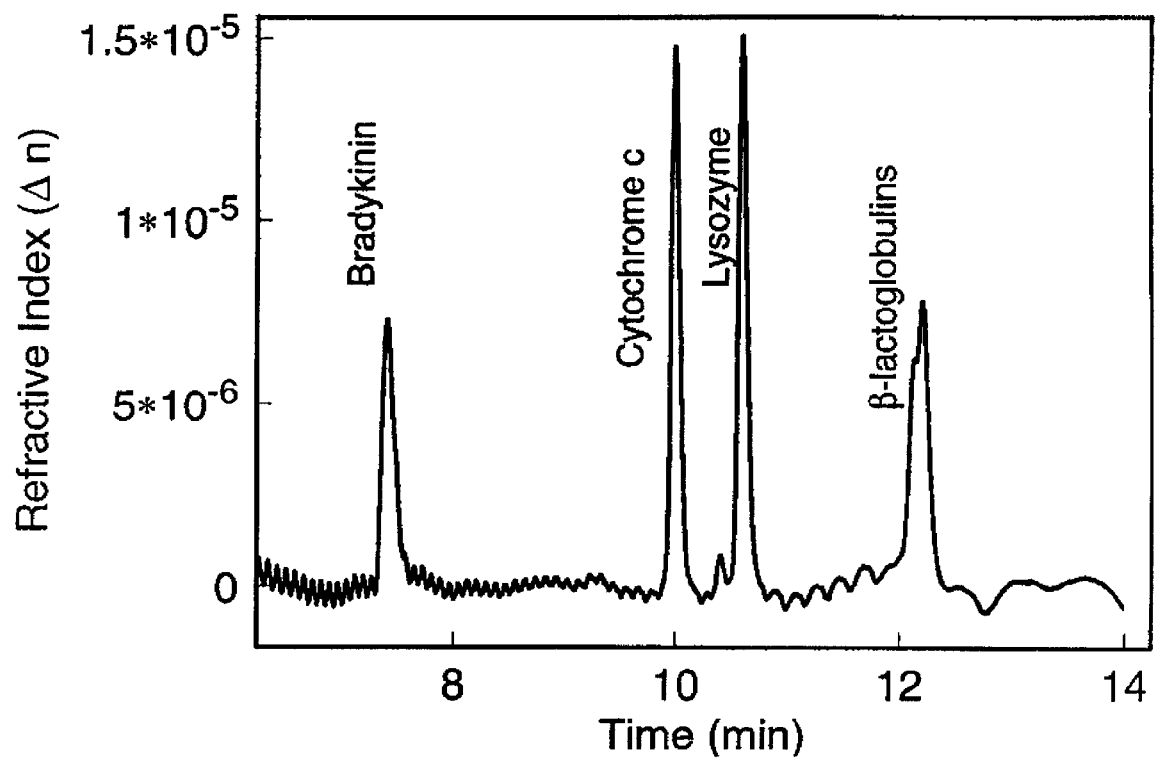
FIG. 5. The chromatogram of FIG. 4 from which has been subtracted the background/gradient signal.

FIG. 3 presents a plot of the refractive index output of the extended range instrument verses time for a sample eluting in a reversed phase chromatography. A linear gradient of water and acetile nitrile produced the elution. The actual sample peaks are hard to discern. If we enlarge the dotted section of FIG. 3, we obtain FIG. 4 wherein the eluting peaks are clearly visable. Subtracting the background gradient yields the final result of FIG. 5.

Stability

Figure 6:
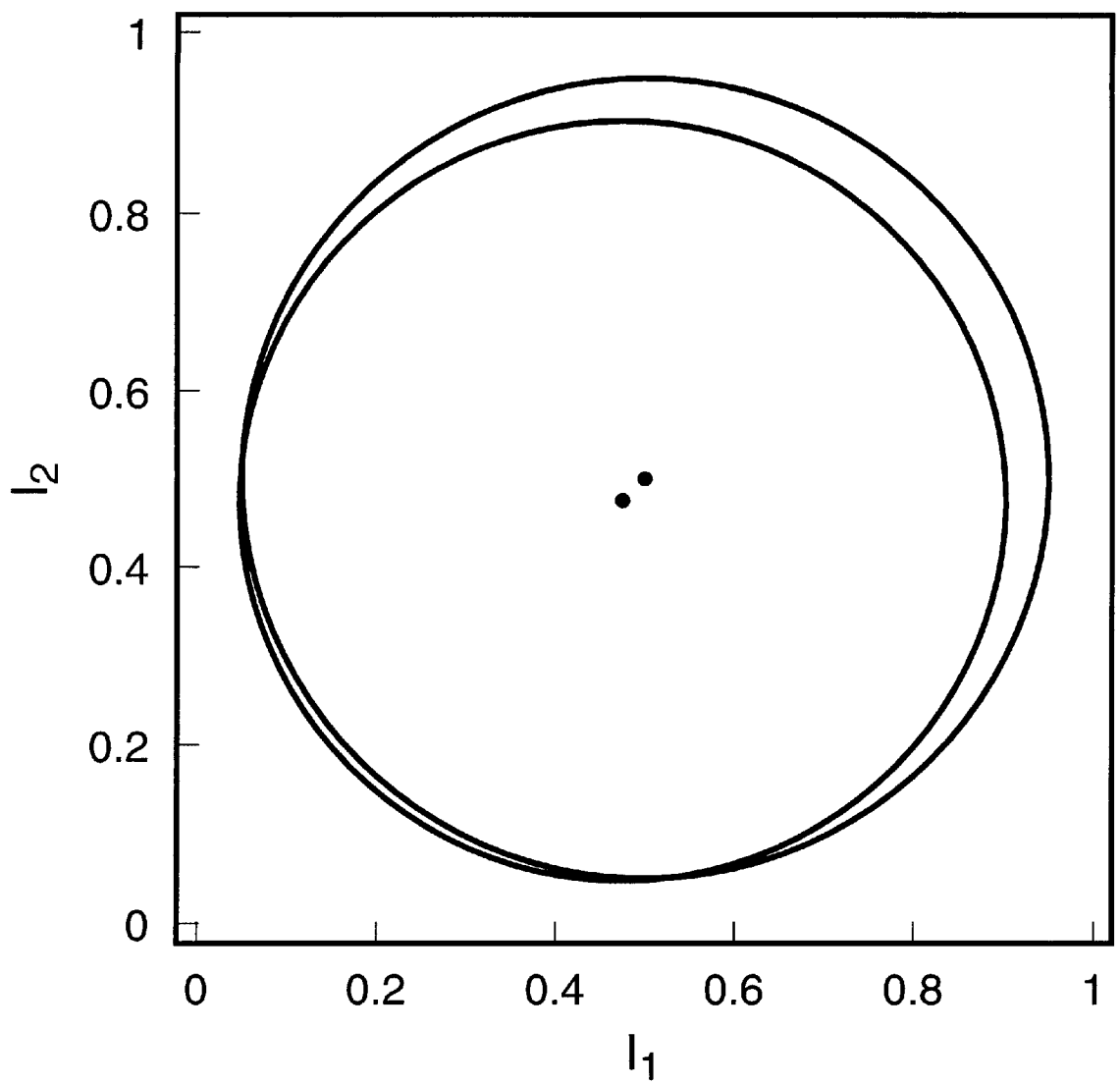
FIG. 6. Relation between two intensity measurements as affected by a change in overall intensity.

Although many light sources are provided with stabilization means or else monitored to provide a reference for all subsequent intensities measured, when intensity drifts occur that are not compensated or when the detectors and/or its associated electronics drifts, there will be signal artifacts that may affect its performance and render its readings erroneous. Let us assume that the intensity of the light source or, equivalently, the detection circuitry, experiences a drift slow compared with the measurement time of the invention. In particular, hours or days may elapse between the calibration of the instrument and the data collection. This will cause the calculation in Eq. (18) to accumulate an error. The best way of understanding the effect of this error is to consider a plot of $I_1$ versus $I_2$ as $I_0$ drifts. From Eq. (17), it is clear that pairs of measurements $(I_1, I_2)$ must lie on a circle with a radius given by $I_0 C_r$, centered on $I_0$. As the intensity decreases, this circle shrinks and the center moves towards the origin. This is illustrated schematically in FIG. 6.

The error in the angle as a function of the change in the intensity can be computed as $$\theta(I_0 + \Delta I_0) = \theta(I_0) + \frac{\Delta I_0}{2} \frac{(I_1 - I_2)}{[2I_0^2 + I_1^2 + I_2^2 - 2I_0(I_1 + I_2)]} + O(\Delta I_0^2), \quad (25)$$

where $\Delta I_0$ is the change in the illumination intensity between the calibration and the measurement. The error occurs because after the drift, the measurement is constrained to lie on the smaller circle, but one is computing the angle by using the center of the original circle as the origin.

Intensity Drift Compensation

The measurement error can be reduced if one has an independent measurement of the intensity as a function of time. However, if the apparent change in the intensity is due to a drift in the photodiode sensor, it is not sufficient to know the true illumination intensity. However, even in the absence of such a measurement, one may extract the intensity from three (or more) measurements of the analyzer intensity with different retardances on the liquid crystal. The formula becomes particularly simple if one has calibrated the retarder so that one has four separate voltages which produce retardances which vary by $\lambda/4$. Denote these voltages $V_n$ such that the liquid crystal produces retardances $$r_n = r(V_n) = r_1 + (n-1)\lambda/4. \quad (26)$$

Let the intensities measured in these four retardance states be denoted by $I_n$. From Eq. (12) one has $$I_n = I_0 \left\{ 1 + C_r \cos\left[2\theta_1 + (n-1)\frac{\pi}{2}\right] \right\}, \quad (27)$$

or written out for the individual values $$I_1 = I_0[1 + C_r \cos(2\theta_1)]$$

$$I_2 = I_0[1 - C_r \sin(2\theta_1)]$$

$$I_3 = I_0[1 - C_r \cos(2\theta_1)]$$

$$I_4 = I_0[1 + C_r \sin(2\theta_1)] \quad (28)$$

Therefore one may extract the current value of the intensity $I_0$ as $$I_0 = \frac{I_1 + I_3}{2} = \frac{I_2 + I_4}{2} = \frac{I_1 + I_2 + I_3 + I_4}{4}. \quad (29)$$

Although the three expressions are in principle equivalent, the last average results in the best noise reduction. Similarly the sine and cosine of the angle can be written in the symmetric form $$\cos(2\theta_1) = \frac{I_1 - I_3}{2I_0 C_r} \quad (30)$$

$$\sin(2\theta_1) = \frac{I_4 - I_2}{2I_0 C_r}.$$

and the angle $\theta_1$ is then computed by the simple expression $$\theta_1 = \arctan(I_4 - I_2, I_1 - I_3)/2. \quad (31)$$

Clearly, this algorithm may be generalized for an arbitrary number of retardance states.

Correction for Time Varying Signal

Equation (31) is the preferred embodiment of the invention provided that intensity or detector drift is slow. However, there remains another source of error whenever a refractive index gradient is present during a measurement. Each measurement of the angle is computed from two (or more) intensity measurements as described above. These measurements are performed sequentially. If one is measuring a sample for which the index is changing in time, it will change between the two measurements giving rise to an error which depends on the rate of change of the refractive index in the sample cell. If this refractive index changes during the collection of the two, or four, intensity values, the resulting errors could be significant. For illustrative purposes, consider the two point measurement. The intensity samples are taken sequentially $I_1(t)$, $I_2(t+\Delta t)$, $I_1(t+2\Delta t)$, $I_2(t+3\Delta t)$, etc. One may correct the error, to first order in $\Delta t$ by time symmetrizing the observations about each incremental interval, $\Delta t$, $2\Delta t$, ..., etc.

$$\tilde{\theta}(\Delta t) = \theta\left(\frac{I_1(t) + I_1(t + 2\Delta t)}{2}, I_2(t + \Delta t)\right) + O(\Delta t^2) \quad (32)$$

$$\tilde{\theta}(2\Delta t) = \theta\left(I_1(t + 2\Delta t), \frac{I_2(t + \Delta t) + I_2(t + 3\Delta t)}{2}\right) + O(\Delta t^2).$$

The notation $\theta(t)$ is the symmetrized angle as a function of time and $\theta(I_1, I_2)$ is the two point formula of Eq. (19). As should be obvious to those skilled in the art, Eq. (32) may be extended similarly to symmetrize the four point result of Eq. (31).

Fast Fringe Counting

As one increases the rate at which $\Delta n/\Delta t$ or, equivalently, $\Delta\theta/\Delta t$ is changing to the point that more than half of a fringe changes between samples, the tracking algorithm described above will fail to count the fringes accurately. However, if the variable retarder is fixed in a single state, the oscillating signal intensity can be monitored at high speed allowing, thereby, fringes to be counted, though any reversal of direction cannot be detected. This could allow the existing Optilab to follow the fringes as they go sweeping by. The extended Optilab uses this as a "fast fringe counting" mode when the index is changing too rapidly to measure accurately such as the leading edge of a large salt pulse. The problem with this method is that a rapid reversal of signal direction cannot be detected. However, in a practical chromatography application, the fringe counting method is used on the steep slope of peaks, reverting to the full analysis as the rate of change slows near the top of the peak.

Other Embodiments of the Invention

Although the preferred embodiment of this invention makes use of a liquid crystal retarder to follow the rotation of the elliptically polarized beam's major axis, there are two other implementations that could achieve this. We will discuss briefly two of these implementations: a split beam structure and a rotating analyzer.

Split Beam

Figure 7:
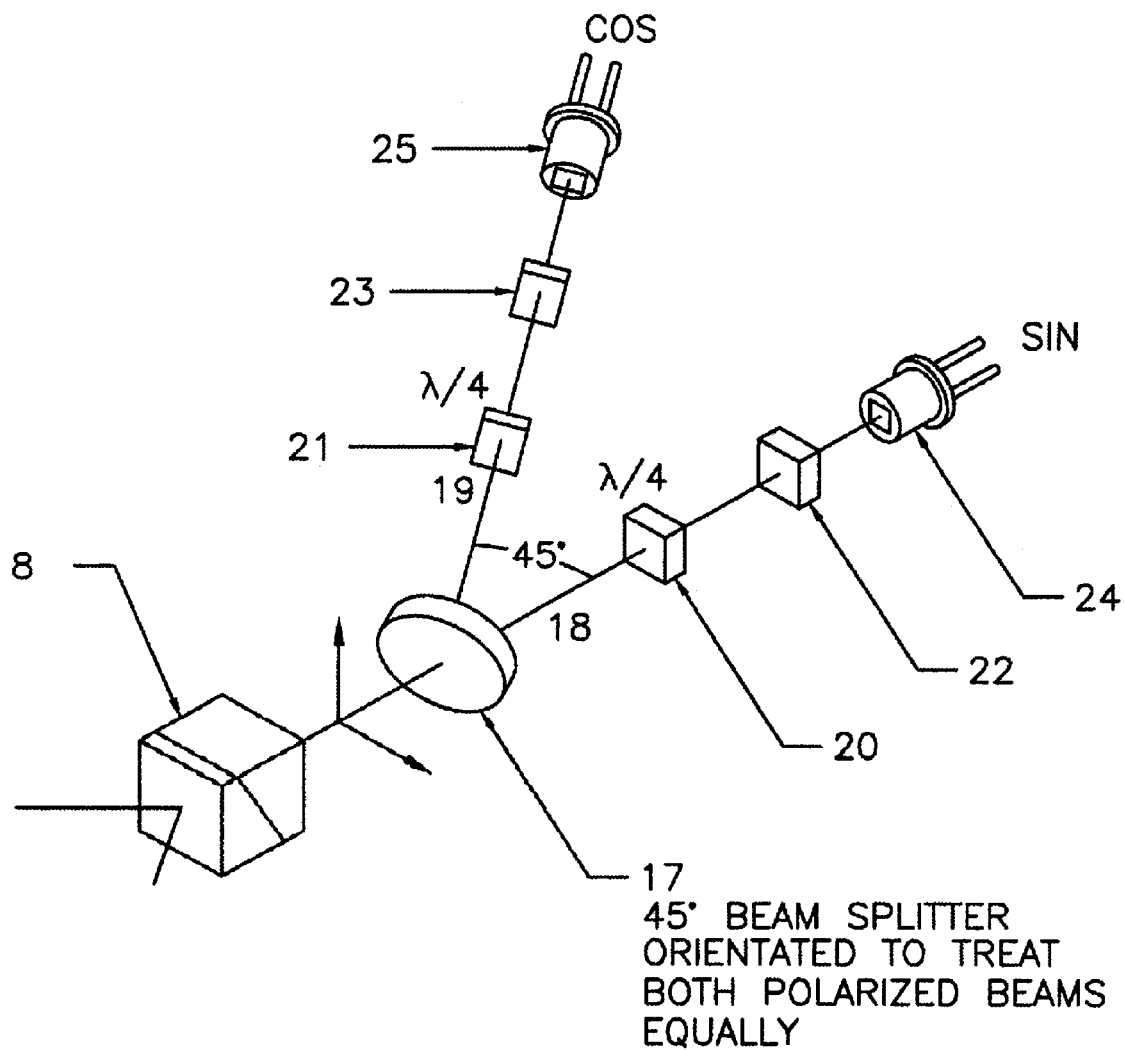
FIG. 7. A split beam configuration for tracking the polarization axis rotation.

FIG. 7 shows the configuration of a split beam implementation to follow the rotation of the emerging combined beam. After the recombined beam emerges from the second Wollaston prism 8, it is split by a partially silvered mirror, prism, or pellicle means 17 into two beams 18 and 19 of nearly equal intensity. Each beam then goes through its own quarter wave plate 20 and 21, polarization analyzer 22 and 23, and detector 24 and 25. The two analyzers are set at 45 degrees physical angle to one another, corresponding to 90 degrees phase in the output signal. The analyzers may be rotated initially to determine the maximum and minimum intensity as described for the liquid crystal retarder configuration, or another means of phase scanning such as a tilted plate or an offset lens may be used to normalize the intensity. In operation, one beam produces a sin $(2\theta_1)$ signal and the other produces a cos $(2\theta_1)$ signal. Although such a configuration requires separate calibration of each detector/analyzer pair, it permits a simultaneous measurement of the two signals without time delay between them and obviating, thereby, the problems associated with the time delays and limitations on tracking speeds of the liquid crystal implementation. In a manner similar to that used in the liquid crystal implementation, the rotation angle $\theta_1$ is calculated from the four quadrant arctangent $$\theta_1 = \arctan(\sin\theta_1, \cos\theta_1)/2 \qquad (32)$$
$$= \arctan(-I_1/I_{01} + 1, I_2/I_{02} - 1)/2,$$

where for the first beam whose measured intensity $I_1$ corresponds to sin $(2\theta_1)$, $I_{10}=(I_{max1}+I_{min1})/2$ and for second beam whose measured intensity $I_2$ corresponds to cos $(2\theta_1)$, $I_{20}=(I_{max2}+I_{min2})/2$. The subsequent analysis which includes the subtraction of the background signal follows exactly the liquid crystal procedure described earlier. The split beam implementation, because it has two detectors and analyzers, can have its own drift problems should either detector's sensitivity change in time. These may be remedied, however, by means, for example, of continuous monitoring of the ratio of the two detectors' average output signal $I_{10}/I_{20}$, as would be obvious to those skilled in the art of such signal processing.

Rotating Polarization Analyzer

Figure 8A:
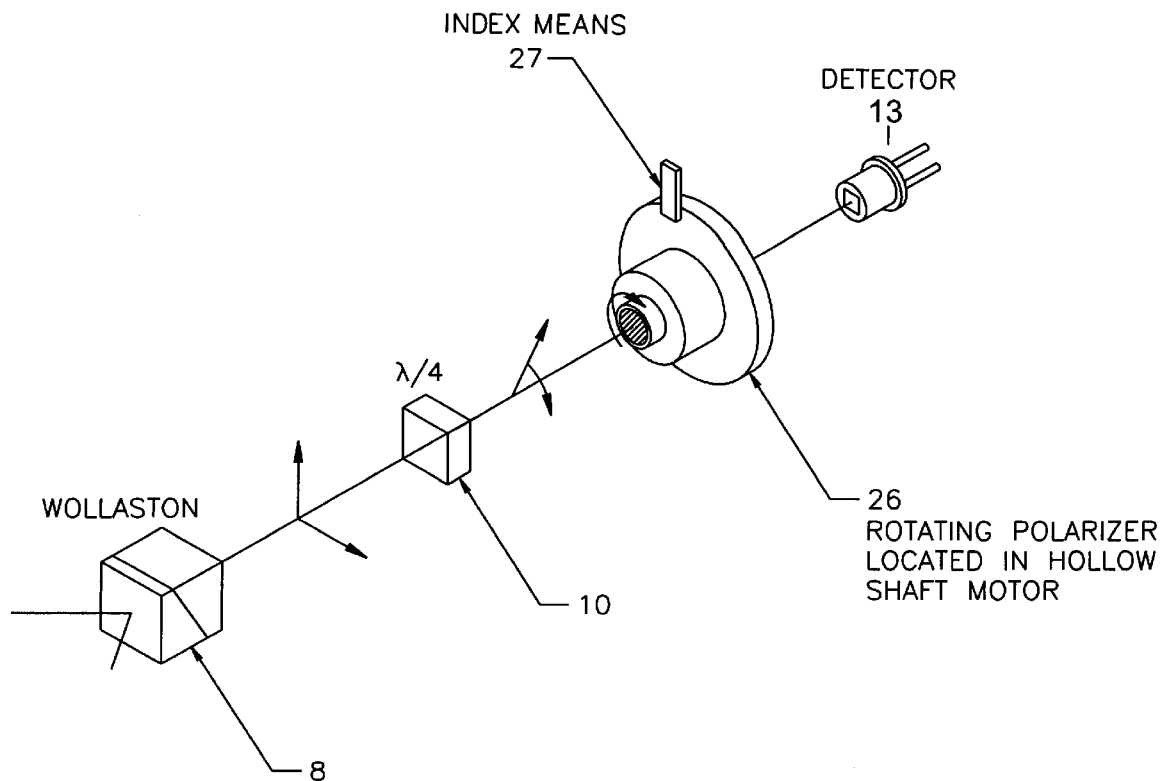
FIG. 8. A rotating analyzer configuration for tracking the polarization axis rotation.
Figure 8B:
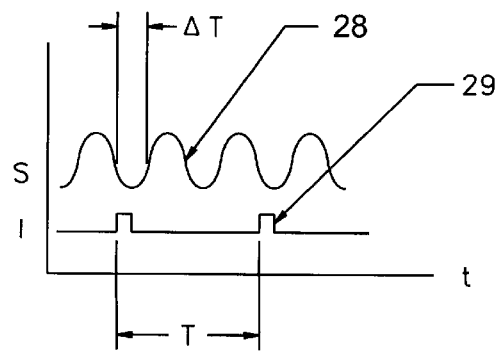

Another implementation to track the output beam rotation is shown in FIG. 8. The polarization analyzer of the Optilab refractometer can be mounted on a hollow shaft motor 26, spinning at a constant rate, for example 600 rpm. An index means 27 can be used to indicate the reference angle of the analyzer, for example, a small magnet rotating with the analyzer and a Hall effect detector. Then the angle increases linearly with time. The wave 28 detected by detector means can easily be viewed on an oscilloscope or preferably digitized and analyzed by computer means using the index 29 as a reference. The 600 rpm spin rate would produce a 20 Hz sine wave which changes phase as the refractive index of the sample changes. Increasing the sample index moves the wave to forward in time and decreasing the index moves it back. Various methods can be used to measure the phase including: a phase locked loop, a zero crossing detector and timer, high speed digital convolutions.

There are many variations of the above invention that will be obvious to those skilled in the art of interferometry. For example, the optical paths of any of the aforementioned embodiments may be folded on themselves, eliminating, thereby, one of the Wollaston prisms and lenses while at the same time doubling the sensitivity of the instrument since, for that case, the path length will be doubled. Such an embodiment will compensate for optical rotation by the sample since the reflected beam will be rotated in the opposite sense. Certainly there are other means which effectively follow the teachings conveyed herein by which measurement of the rotation of the major axis of a light beam relative to an arbitrary reference angle may be used to determine quantitatively the corresponding changes in refractive index of a sample.

We claim:

1. A method for measuring the refractive index difference, $\Delta n$, of two solutions contained, respectively, in two separate optical cells of equal length L, one of which contains a reference solution and the other a sample solution comprising the steps of a) producing a plane polarized beam of monochromatic light incident normally on a Wollaston prism means and whose plane of polarization lies at 45° to a principal optical axis thereof;

b) passing both of the two beams leaving said Wollaston prism through a lens means so as to direct one said beam whose polarization is vertical through said sample cell and the other said beam whose polarization is horizontal through said reference cell;

c) superimposing said two beams upon their leaving said cells by lens means at a second Wollaston prism means; said superimposed beam emerging therefrom;

d) passing said emerging beam of (c) through a liquid crystal retarder means whose fast axis is aligned with said vertically polarized beam that had passed through said sample cell;

e) inserting after said liquid crystal retarder means and normal to the beam emerging therefrom sequentially a quarter waveplate means, a plane polarizing analyzer means, and a light detector means, whereby said superimposed beam emerging from said quarter waveplate is a superposition of two counter rotating circularly polarized beams producing an essentially plane polarized resultant beam whose plane of polarization has been rotated with respect to the 45° plane of polarization of said incident beam of step (a);

f) changing the voltage applied to said liquid crystal retarder to measure thereby at said detector means the maximum ad minimum intensity, $I_{max}$ and $I_{min}$, respectively, corresponding to a phase difference π, of said beam emerging therefrom;

g) calibrating said liquid crystal retarder by selecting two applied voltages producing two corresponding retardance states whose difference therebetween is exactly $\pi/2$;

h) applying sequentially, and at a frequency sufficient to insure that said plane of polarization does not rotate more than $\pi/2$ while said retarder switches between said two retardance states, said two voltages and measuring with said detector means the intensities $I_1$ and $I_2$, respectively, after each corresponding voltage has been applied sequentially thereto;

i) determining said rotation angle of said plane polarized resultant beam of step (e) by performing the four quadrant arctangent $$\theta_1 = \arctan[\sin(2\theta_1), \cos(2\theta_1)]/2$$
$$= \arctan[-I_2/I_0 + 1, I_1/I_0 - 1]/2$$

where the intensity $I_0$ is defined as $$I_0 = (I_{max} + I_{min})/2;$$

and j) calculating said refractive index difference, $\Delta n$, of said two solutions from $$\theta_1 = \pi \Delta n L/\lambda,$$

where L is The length of each of said cells and $\lambda$ is the wavelength in vacuum of said incident plane polarized beam of light.

2. The method of claim 1 where the retarder calibration at the two states of step g is replaced by calibrating the retarder at four states, each differing by $\pi/4$ and, thereby, making intensity measurements $I_1$, $I_2$, $I_3$ and $I_4$ corresponding to angles $$\theta_n = \theta + \theta_r + (n-1)\pi/4, n=1 \text{ to } 4$$

and calculating said angle $\theta_1$ from the four quadrant arctangent $$\theta_1 = \arctan(I_4 - I_2, I_1 - I_3)/2.$$

3. The method of claim 1 where said source of said polarized light beam incident normally on said Wollaston prism of step (a) is a laser.

4. The method of claim 1 where the source of said polarized light beam incident normally on said Wollaston prism of step (a) is a continuous light source in combination with an interference filter placed before said detector to select a single wavelength.

5. The method of claim 1 where the calculation of the angle $\theta_1$ is made by first symmetrizing the intensity measurements about each time increment $\Delta t$, corresponding to the time interval between measurements at the two states of said liquid crystal retarder.

6. The method of claim 2 where the calculation of the angle $\theta_1$ is made by first symmetrizing the intensity measurements about each time increment $3\Delta t$, where $\Delta t$ corresponds to the time interval between the measurement of each of the four states of said liquid crystal retarder.

7. The method of claim 1 where said incident light beam is from a laser.

8. The method of claim 1 where said incident light beam is from a continuous light source and where a narrow waveband filter is inserted between said liquid crystal retarder and said detector means, selecting thereby said measurement wavelength $\lambda$.

9. The method of claim 1 where said liquid crystal retarder is calibrated by means of four applied voltages producing four corresponding retardance states whose difference therebetween each is exactly $\pi/2$.

10. An interferometric refractometer for measuring the refractive index difference, $\Delta n$, of two solutions contained, respectively, in two separate optical cells of equal length L, one of which contains a reference solution and the other a sample solution, comprised of the following elements:

a) a monochromatic light source producing a fine beam of light incident upon b) a polarizer producing a plane polarized beam of light whose plane of polarization lies at 45° to a principal optical axis on c) a first Wollaston prism upon which said beam of polarized light is incident normally and through which emerge therefrom two diverging beams, one of which is polarized vertically and the other of which is polarized horizontally;

d) a single lens to direct said beam whose polarization is vertical through said sample cell and to direct other said beam whose polarization is horizontal through said reference cell;

e) a second lens to combine both beams, after they emerge from their respective cells, at f) a second Wollaston prism followed by g) a calibrated liquid crystal retarder whose fast axis is aligned with said vertically polarized beam that has passed through said sample cell and through which said combined beam emerging from said second Wollaston prism passes; said calibration consisting of selecting two applied voltages producing two corresponding retardance states whose difference therebetween is exactly $\lambda/2$; followed by h) a quarter waveplate, followed by i) a plane polarizing analyzer, and j) a light detector means, whereby said superimposed beam emerging from said quarter waveplate is a superposition of two counter rotating circularly polarized beams producing an essentially plane polarized resultant beam whose plane of polarization has been rotated with respect to the 45° plane of polarization of said incident beam of step (b);

k) a variable and controlled voltage source applied to said liquid crystal retarder to allow measurement thereby at said detector the maximum and minimum intensity, $I_{max}$ and $I_{min}$, respectively, corresponding to a phase difference $\pi$, of said beam emerging therefrom;

l) means to determine said rotation angle of said plane polarized resultant beam of step (j) by performing the four quadrant arctangent $$\theta_1 = \arctan[\sin(2\theta_1), \cos(2\theta_1)]/2$$
$$= \arctan[-I_2/I_0 + 1, I_1/I_0 - 1]/2$$

where the intensity $I_0$ is defined as $$I_0 = (I_{max} + I_{min})/2;$$

and m) means to calculate said refractive index difference, $\Delta n$, of said two solutions from $\theta_1 = \pi \Delta n L / \lambda,$ where L is the length of each of said cells and $\lambda$ is the wavelength in vacuum of said incident plane polarized beam of light.

11. The interferometric refractometer of claim 10 where said monochromatic light source is a laser.

12. The interferometric refractometer of claim 11 where said laser produces plane polarized light oriented at 45° to a principal optical axis of said first Wollaston prism and said polarizer of (b) is absent.

13. The interferometric refractometer of claim 10 where said incident light beam is from a continuous light source and where a narrow waveband filter is inserted between said liquid crystal retarder and said detector means, selecting thereby said measurement wavelength $\lambda$.

14. The interferometric refractometer of claim 10 where said liquid crystal retarder is calibrated by means of four applied voltages producing four corresponding retardance states whose difference therebetween each is exactly $\pi/2$.

15. The interferometric refractometer of claim 10 where said calibrated liquid crystal retarder element (g) is absent, the plane polarizing analyzer element (i) is replaced by an axially rotating polarizing analyzer, and elements (h), (i), and (j) are replaced by an indexing means producing a signal that may be used to follow the phase change $\Delta\phi$ of said signal at said detector means; with said phase change $\Delta\phi$ used to determine said refractive index difference $\Delta n$ from relation $\Delta n = \lambda \phi / (2\pi \Delta n L)$.

16. An interferometric refractometer for measuring the refractive index difference, $\Delta n$, of two solutions contained, respectively, in two separate optical cells of equal length L, one of which contains a reference solution and the other a sample solution, comprised of the following elements:

a) a monochromatic light source producing a fine beam of light incident upon b) a polarizer producing a plane polarized beam of light whose plane of polarization lies at 45° to a principal optical axis on c) a first Wollaston prism upon which said beam of polarized light is incident normally and through which emerge therefrom two diverging beams, one of which is polarized vertically and the other of which is polarized horizontally;

d) a single lens to direct said beam whose polarization is vertical through said sample cell and to direct other said beam whose polarization is horizontal through said reference cell;

e) a second lens to combine both beams, after they emerge from their respective cells, at f) a second Wollaston prism followed by g) a beam splitter means producing two beams, A and B, of nearly equal intensity each incident upon a different quarter waveplate followed by h) a quarter wave plate followed by i) a plane polarizing analyzer, and j) a light detector means, whereby the optical axes of said polarizing analyzer are oriented to be 45 degrees rotated one with the other measured with respect to a normal to the plane transverse to the planes of said polarizing analyzers in which both beams lie k) Means to detect the maximum $I_{max}$ the minimum $I_{min}$ intensities incident respectively at each detector for each said beam A and B and to normalize the intensity of each thereby.

17. The interferometric refractometer of claim 16 where said monochromatic light source is a laser.

18. The interferometric refractometer of claim 17 where said laser produces plane polarized light oriented at 45° to a principal optical axis of said first Wollaston prism and said polarizer of (b) is absent.

19. The interferometric refractometer of claim 17 where said incident light beam is from a continuous light source and where a narrow waveband filter is inserted between said each said polarizing analyzer and said following detector means, selecting thereby said measurement wavelength $\lambda$.

* * * * *

UNITED STATES PATENT AND TRADEMARK OFFICE
CERTIFICATE OF CORRECTION

PATENT NO. : 6,128,080
DATED : October 3, 2000
INVENTOR(S) : Gary R. Janik, Douglas W. Shepard, Steven P. Trainoff, David T. Phillips It is certified that error appears in the above-identified patent and that said Letters Patent is hereby corrected as shown below:

The order of inventors should read:

Steven P. Trainoff, Carpinteria California
David T. Phillips, SantaBarbara California
Gary R. Janik, Palo Alto California
Douglas W. Shepard, Santa Barbara, California Signed and Sealed this Nineteenth Day of June, 2001

*Attest:*

NICHOLAS P. GODICI
*Attesting Officer*  *Acting Director of the United States Patent and Trademark Office*